US011147765B1

(12) United States Patent
Badr-Eldin et al.

(10) Patent No.: US 11,147,765 B1
(45) Date of Patent: *Oct. 19, 2021

(54) INSTANTLY DISSOLVING BUCCAL FILMS (71) Applicant: King Abdulaziz University, Jeddah (SA)

(72) Inventors: Shaimaa M. Badr-Eldin, Jeddah (SA); Hibah M. Aldawsari, Jeddah (SA); Abdelsattar Omar, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/187,915

(22) Filed: Mar. 1, 2021

Related U.S. Application Data (63) Continuation-in-part of application No. 16/934,081, filed on Jul. 21, 2020, now Pat. No. 10,973,760.

(51) Int. Cl.
| | | |
|---|---|---|
| *A61K 9/00* | (2006.01) | |
| *A61K 47/40* | (2006.01) | |
| *A61K 47/38* | (2006.01) | |
| *A61K 47/10* | (2017.01) | |
| *A61K 47/36* | (2006.01) | |
| *A61K 31/138* | (2006.01) | |
| *A61K 47/12* | (2006.01) | |

(52) U.S. Cl.
CPC ............ *A61K 9/006* (2013.01); *A61K 31/138* (2013.01); *A61K 47/10* (2013.01); *A61K 47/12* (2013.01); *A61K 47/36* (2013.01); *A61K 47/38* (2013.01); *A61K 47/40* (2013.01)

(58) Field of Classification Search
None
See application file for complete search history.

(56) References Cited

U.S. PATENT DOCUMENTS

2015/0202168 A1* 7/2015 Turkyilmaz ........... A61K 47/12
424/400
2016/0206641 A1* 7/2016 Singh ..................... A61K 47/40

OTHER PUBLICATIONS

ElMeshad et al., "Characterization and Optimization of Orodispersible Mosapride Film Formulations", AAPS PharmSciTech, 12(4), 2011, pp. 1384-1392. (Year: 2011).*

* cited by examiner

Primary Examiner — Melissa L Fisher
(74) Attorney, Agent, or Firm — W & C IP (57) ABSTRACT

Instantly dissolving buccal fims comprising certain pH modifiers, film formers, film modifiers, and solubilizing agents are provided. Methods of providing the buccal film to enhance the dissolution and bioavailability of low solubility basic drugs, such as dapoxetine hydrochloride, in a subject are also provided.

12 Claims, 4 Drawing Sheets

INSTANTLY DISSOLVING BUCCAL FILMS

FIELD OF THE INVENTION

The invention is generally related to instantly dissolving buccal films which are useful for enhancing the dissolution and bioavailability of low solubility basic drugs, such as dapoxetine, at the neutral pH of body fluids.

BACKGROUND OF THE INVENTION

Intraoral delivery systems (IODSs) have been used as a promising strategy to surmount the problems associated with oral drug administration. These dosage forms offer the advantages of easy administration and rapid action as they disintegrate or dissolve rapidly in the mouth. In addition, direct absorption of drugs into the systemic circulation could be achieved via the buccal mucosa, thus bypassing hepatic first pass [1]. Instantly disintegrating or dissolving tablets (IDT) have been introduced as the first IODSs for patients who suffer from dysphagia. They are characterized by their rapid disintegration and/or dissolution; however, they have some drawbacks such as difficult handling owing to their fragility. Accordingly, instantly dissolving buccal films have been introduced recently as an alternative to surpass the limitations associated with instantly dissolving tablets [2-4].

Instantly dissolving buccal films (IDBFs) are hydrocolloid based films that readily dissolve upon contact with the salivary fluid. They have recently gained attention due to enhanced patient compliance and capability of surmounting the problem of hepatic first pass of many drugs [5,6]. However, intraoral administration of poorly soluble drugs poses a great challenge for their buccal absorption. Several approaches have been utilized for enhancing the dissolution of drugs including solid dispersion with water soluble polymers, binary systems with cyclodextrins [7], use of surfactants [8] and pH modifiers [9].

Dapoxetine hydrochloride (DPX) is a selective serotonin reuptake inhibitor for depression treatment. It was recently approved as an oral treatment for premature ejaculation (PE) to be the first selective serotonin reuptake inhibitor approved for this function [22,23], however, DPX has an oral bioavailability of 42% owing to its significant hepatic first pass metabolism [24]. DPX presystemic metabolism represents a challenging limitation for oral administration of the drug and foreshadows the potential of utilizing transmucosal route for enhancing the drug's bioavailability [25]. However, DPX is a weakly basic drug with a pH dependent solubility that could limit its dissolution in the body's neutral fluids and subsequent absorption via mucosal barriers [26].

Transmucosal delivery of DPX via sublingual and intranasal mucosa has been investigated by Fouad et al. [26,27] who developed DPX loaded instantly-soluble matrix and instantly-dispersible nanocarrier powder systems. In addition, buccal delivery of DPX has been investigated by Liew and Peh [28] who developed DPX orally disintegrating tablets and El-Refai et al. [29] who developed vardenafil hydrochloride/DPX hydrochloride orodispersible tablets. However, no attempts were reported for the formulation of dissolvable buccal films of DPX.

Due to the bioavailability problems with delivery of basic drugs, alternative and effective drug delivery systems are needed.

SUMMARY

An aspect of the disclosure provides an instantly dissolving buccal film comprising: a pH modifier such as tartaric acid, a solubilizing agent such as hydroxypropyl beta cyclodextrin, a film former such as hydroxypropyl methylcellulose (HPMC), a film modifier such as maltodextrin, and a low solubility drug such as dapoxetine hydrochloride.

In some embodiments, the film comprises 1-5% propylene glycol. In some embodiments, the ratio of HPMC to maltodextrin is from 1:3 to 3:1. In some embodiments, the ratio of HPMC to maltodextrin is 1:1. In some embodiments, the maltodextrin has a dextrose equivalent value of 16.5-19.5. In some embodiments, the film comprises 25-35 mg of dapoxetine hydrochloride.

Another aspect of the disclosure provides a method of improving bioavailability of a low solubility drug such as dapoxetine hydrochloride, comprising providing to a subject in need thereof an instantly dissolving film as described herein.

DETAILED DESCRIPTION

Embodiments of the disclosure provide oral film formulations that improve the bioavailability of low solubility basic drugs. The hydrophilic polymer-based films provide a rapid onset of action via enhanced drug dissolution in the salivary pH. The formulations described herein comprise certain pH modifiers, film formers, film modifiers, and solubilizing agents that have improved pharmacokinetic behavior, particularly in comparison to oral tablet formulations.

The term "film" includes thin films and sheets, in any shape, including rectangular, square, or other desired shape. The films described herein may be any desired thickness and size such that it may be placed into the oral cavity of the user. For example, the films may have a relatively thin thickness of from about 1 to about 300 μm, or they may have a somewhat thicker thickness of from about 300 to about 800 μm. For some films, the thickness may be even larger Films may be in a single layer or they may be multi-layered, including laminated films.

"Instantly dissolving" or "rapidly dissolving" oral or buccal films refers to films that quickly dissolve or disintegrate in the saliva within seconds without the need for water or chewing. In some embodiments, the film has a dissolving time of 30 seconds or less, e.g. 20, 15, or 10 seconds or less.

The solubilizing agent as described herein may comprise a hydrophilic cyclodextrin. Cyclodextrins are a group of compounds consisting of, or derived from, the three parent cyclodextrins—alpha-, beta- and gamma-cyclodextrins. Alpha-, beta- and gamma-cyclodextrins are simple oligosaccharides consisting of six, seven, or eight glucose residues, respectively, connected to macrocyles by alpha (1 to 4) glycosidic bonds. Each of the glucose residues of a cyclodextrin contains one primary (O6) and two secondary hydroxyls (O2 and O3) which can be substituted, for example, methylated. Many cyclodextrin preparations in practical use are mixtures of chemically individual derivatives in which only a part of hydroxyl groups were substituted and which differ in number and position of these substituents. Their solubilizing action is achieved via the formation of partial or complete inclusion complexes. Cyclodextrins also have surfactant-like properties that could promote wetting and dissolution of poorly soluble drugs. Cyclodextrins are also advantageously biodegradable, non-toxic, and biocompatible. In some embodiments, the solubilizing agent is beta cyclodextrin or hydroxypropyl beta cyclodextrin. In some embodiments, the amount of solubilizing agent incorporated into the formulation is 20-40 mg, e.g. 25-35 mg, e.g. about 30 mg.

Polymers are responsible for imparting adequate mechanical properties to films, and they affect the film dissolution and/or disintegration within the buccal cavity, and consequently the liberation of the drug. Maltodextrins, a film modifier, are mixtures of poly- and oligo-saccharides produced by starch hydrolysis that vary in their dextrose equivalent value. In some embodiments, the maltodextrin has a dextrose equivalent value of 16.5-19.5. Other suitable film modifiers include, but are not limited to, xanthan gum, guar gum, carrageenan, and polyhydric alcohols such as mannitol, sorbitol and xylitol. In some embodiments, the amount of film modifier incorporated into the formulation is 40-200 mg, e.g. 60-180 mg, e.g. 80-140 mg, e.g. about 120 mg.

Suitable film formers include, but are not limited to, water-soluble polymers such as hydroxyethylcellulose, hydroxypropylcellulose, hydroxypropyl methylcellulose (HPMC), and a water-soluble salt of carboxymethylcellulose (for example sodium carboxymethyl cellulose) pullulan, etc. In some embodiments, the amount of film former incorporated into the formulation is 40-200 mg, e.g. 60-180 mg, e.g. 80-140 mg, e.g. about 120 mg.

In some embodiments, the ratio of film former (e.g. HPMC) to film modifier (e.g. maltodextrin) is from 1:3 to 3:1, for example 1:1.

A pH modifier alters the microenvironmental pH of the drug particles to a pH that allows for easy dissolution of the drug. The pH modifier or acidifier as described herein may be an organic acid or inorganic acid. Suitable organic acids include, but are not limited to, tartaric acid, malic acid, citric acid, acetic acid, propionic acid, glycolic acid, pyruvic acid, oxalic acid, malonic acid, succinic acid, maleic acid, fumaric acid, benzoic acid, cinnamic acid, mandelic acid, methanesulfonic acid, ethanesulfonic acid, p-toluenesulfonic acid, or salicylic acid. Inorganic acids include, but are not limited to, hydrochloric acid, hydrobromic acid, sulfuric acid, nitric acid, or phosphoric acid. In some embodiments, the amount of pH modifier, e.g. tartaric acid, incorporated into the formulation is 5-100 mg, e.g. 25-35 mg, e.g. about 30 mg.

The film may further comprise one or more plasticizers such as propylene glycol or glycerin. Other suitable plasticizers include glycerol, polyethylene glycols (PEG), castor oil, dibutyl phthalate, and sorbitol. In some embodiments, the film comprises 1-5% plasticizer.

The present disclosure provides the use of an instantly dissolving buccal film as described herein for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is a low solubility basic drug such as dapoxetine hydrochloride, quinidine, chlorpromazine, propranolol, and diazepam. In some embodiments, the amount of active agent incorporated into the formulation is 5-100 mg, e.g. 25-35 mg.

The film as described herein may be prepared by utilizing a selected casting or deposition method and a controlled drying process according to methods known in the art. For example, the film may be prepared through controlled drying processes, which include application of heat and/or radiation energy to the wet film matrix to form a viscoelastic structure, thereby controlling the uniformity of content of the film. Alternatively, the films may be extruded according to methods known in the art.

The films of the present disclosure may also contain other components such as, but not limited to, additives, adjuvants, buffers, tonicity agents, and preservatives. An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, saccharin trehalose, mannose, D-galactose, and lactose and flavorings such as orange oil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

The present disclosure also provides a method of treatment of a human or non-human animal subject by delivery of a substantially insoluble or sparingly soluble biologically active agent, said method comprising administering to said subject a film of the disclosure as hereinbefore defined. Administration of the films described herein provides for enhanced or improved dissolution and bioavailability of the drug.

The compositions and dosage forms of the disclosure may be useful for the treatment of any disease or disorder that the included active agent is useful for treating. For example, if dapoxetine is used, the composition or dosage form may be useful for the treatment of depression or premature ejaculation. In an embodiment, the film of the disclosure is applied topically to any mucosal tissue, e.g. to the buccal, palatal, gingival, lingual, sublingual or cheek mucosa of the buccal cavity.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. dapoxetine) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

As used herein, the term "about" refers to a range of values ±10% of a specified value. For example, the phrase "about 200" includes ±10% of 200, or from 180 to 220.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

Summary

Dapoxetine (D) is a selective serotonin reuptake inhibitor (S SRI) that was approved for the treatment of premature ejaculation. Dapoxetine hydrochloride (DPX) has a low oral bioavailability due to significant hepatic first pass metabolism. In addition, DPX is a weakly basic drug with a pH dependent solubility that could limit its dissolution in the body neutral fluids. The low solubility at the neutral pH of the body fluids could limit its transmucosal absorption from different body cavities. Thus, this work aimed at enhancing the dissolution of the drug in the neutral pH of body fluids utilizing instantly dissolving buccal films. To surpass these challenges, this work aimed at enhancing DPX bioavailability via the formulation of instantly dissolving buccal films comprising a pH modifier and a hydrophilic cyclodextrin. Tartaric acid and hydroxypropyl beta-cyclodextrin were selected as dual solubilizing agents based on the screening study. $3^2$ factorial design was employed for the formulation and optimization of DPX films. Statistical analysis revealed that hydroxypropyl methyl cellulose E5:maltodextrin ratio and propylene glycol concentrations have significant effects on mechanical properties, percent DPX dissolved after 5 minutes, and in vivo mouth dissolving time at P<0.05. The optimized film [HPMC E5:MDX, 1:1 and 1% PG] showed no significant change of properties or drug dissolution upon storage at 40° C./75% RH for a period of 3 months. In addition, the optimized film showed significantly enhanced absorption relative to the oral reference tablet. Therefore, the optimized film is a new delivery system for DPX with enhanced pharmacokinetic performance.

Material and Methods

Material

Dapoxetine hydrochloride (DPX) was a gift from Spimaco (Riyadh, Saudi Arabia). Hydroxypropyl methyl cellulose E5 (HPMC E5), maltodextrin (MDX, dextrose equivalent 16.5-19.5), propylene glycol (PG), ethanol, citric acid (CA), malic acid (MA), L-tartaric acid (TA), saccharin, beta-cyclodextrin (β-CD, MW=1135 Da), hydroxypropyl beta-cyclodextrin (HP-β-CD, average degree of substitution=0.8 and MW=1460 Da) and orange oil were purchased from Sigma Aldrich (St. Louis, Mo., USA). High-performance liquid chromatography (HPLC) grade acetonitrile were purchased from Merck (Darmstadt, Germany) All other reagents and chemicals were of analytical grade.

Screening of Organic Acids and Cyclodextrins for Enhancing Dissolution of DPX

Various organic acids (CA, MA, and TA) and cyclodextrins β3-CD and HP-β-CD) were assessed as acidifiers and hydrophilic solubilizers to enhance the dissolution of DPX. Equivalent amounts of DPX and each of the studied excipients were thoroughly mixed for 5 min. The dissolution behavior of specified quantity of each mixture equivalent to 30 mg DPX was done in 900 mL phosphate buffer (pH 6.8) using USP Dissolution Tester, apparatus II (DT 720, Erweka, Germany) operating at 50 rpm at 37±0.5° C. [26]. Aliquot samples were withdrawn after 2 and 15 minutes and replaced with equal volume of fresh buffer. Samples were filtered through a 0.22 μm Millipore filter, and the concentration of DPX was quantified spectrophotometrically at 292 nm (UV-2600 PC; Shimadzu, Kyoto, Japan). The dissolution study was done in triplicate.

Preparation of DPX Instantly Dissolving Buccal Films (IDBFs)

Solvent casting technique was utilized to prepare IDBFs containing 30 mg DPX per dosage unit. In all formulations, TA and HP-β-CD were used as acidifier and hydrophilic solubilizer, respectively. Orange oil and saccharin were used as flavoring and sweetening agents, respectively, at a concentration of 0.2% each. The total concentration of HPMC and MDX was kept constant at 16%. In addition, ethanol was added at a concentration of 15% to all formulations. All percentages are expressed relative to the total dispersion. Briefly, specified quantities of HPMC, MDX, PG, and saccharin were dispersed in specified volume of distilled water (8 mL) with added ethanol (2.25 mL), and the volume was then completed to 15 ml. The prepared mixture was stirred at 70° C. for 45 min, and then cooled down to 40° C. Subsequently, a mixture of equal amounts of DPX, HP-β-CD, and TA were stirred into the polymer solution, and then orange oil alcoholic solution was added. 10 mL of the mixture was poured into glass Petri dish (d=5 cm) and left to dry in thermal oven adjusted to 40° C. overnight. The dried films were split into 1×3 cm strips (3 cm$^2$), each containing 30 mg drug. The strips were placed individually in air-tight containers and stored in desiccators over $CaCl_2$ at ambient temperature until further studies. The composition of each of the formulations is provided in Table 1.

TABLE 1

Composition of DPX buccal films

| Run | HPMC* | MDX* | PG** | TA* | CD* |
|---|---|---|---|---|---|
| F1 | 60 | 180 | 15 | 30 | 30 |
| F2 | 60 | 180 | 45 | 30 | 30 |
| F3 | 60 | 180 | 75 | 30 | 30 |
| F4 | 120 | 120 | 15 | 30 | 30 |
| F5 | 120 | 120 | 45 | 30 | 30 |
| F6 | 120 | 120 | 75 | 30 | 30 |
| F7 | 180 | 60 | 15 | 30 | 30 |
| F8 | 180 | 60 | 45 | 30 | 30 |
| F9 | 180 | 60 | 75 | 30 | 30 |

*The amounts in mg per unit dosage form (3 cm$^2$ strip) containing 30 mg drug

**The amounts in μL per unit dosage form (3 cm$^2$ strip) containing 30 mg drug $3^2$ Factorial Design for Formulation and Optimization of DPX Instantly Dissolving Buccal Films Preliminary studies were conducted to assess the effect of using various ratios of the film-forming polymer (HPMC E5) and the film modifier (MDX) on the IDBFs properties. The use of different concentrations of either glycerin or PG as a plasticizer was also investigated. The preliminary films were inspected for ability to peel, stickiness, surface perfection, and in vivo disintegration. According to the results, a $3^2$ factorial design was utilized to explore the effect of the independent variables; HPMC E5:MDX ratio ($X_1$) and PG percentage ($X_2$). Each factor was studied at three levels and a total of nine formulations were prepared, Tables 2 and 3.

TABLE 2

Independent variables and responses used in $3^2$ full factorial experimental design for the formulation and optimization of DPX instantly dissolving buccal films.

| Independent variables | Levels | | |
|---|---|---|---|
| | (−1) | (0) | (+1) |
| $X_1$: HPMC E5: MDX (w/w) | 1:3 | 1:1 | 3:1 |
| $X_2$: PG % | 1.00 | 3.00 | 5.00 |
| Responses | Desirability constraints | | |
| $Y_1$: TS (MPa) | Minimize | | |
| $Y_2$: % E (%) | Maximize | | |
| $Y_3$: EM (MPa) | Minimize | | |
| $Y_3$: % $D_{5min}$ (%) | Maximize | | |
| $Y_3$: In vivo MDT (sec) | Minimize | | |

HPMC E5; Hydroxypropyl methyl cellulose E5, PG; Propylene glycol TS; Tensile strength, % E; Percent elongation at break, EM; Elastic (Young's) modulus, % $D_{5min}$; Percent drug dissolved after 5 min, In vivo MDT; In vivo mouth dissolving time

TABLE 3

Composition and responses of dapoxetine hydrochloride instantly dissolving buccal films prepared according $3^2$ full factorial design.

| | Independent Variables | | Responses (Dependent Variable) | | | | |
|---|---|---|---|---|---|---|---|
| Run | HPMC E5: MDX (w/w, $X_1$)* | PG (%, $X_2$) | TS $ (MPa, $Y_1$) | % E $ (%, $Y_2$) | EM $ (MPa, $Y_3$) | $D_{5\ min}$ # (%, $Y_4$) | MDT # (sec, $Y_5$) |
| F1 | 1:3 | 1.00 | 0.217 ± 0.014 | 147.97 ± 2.56 | 0.146 ± 0.009 | 84.76 ± 3.98 | 9.67 ± 0.56 |
| F2 | 1:3 | 3.00 | 0.434 ± 0.038 | 235.68 ± 5.14 | 0.184 ± 0.019 | 75.97 ± 4.23 | 14.32 ± 1.78 |
| F3 | 1:3 | 5.00 | 0.567 ± 0.043 | 273.88 ± 2.14 | 0.207 ± 0.031 | 71.21 ± 2.11 | 12.89 ± 0.78 |
| F4 | 1:1 | 1.00 | 0.811 ± 0.077 | 115.34 ± 1.56 | 0.703 ± 0.065 | 66.91 ± 2.45 | 13.15 ± 1.77 |
| F5 | 1:1 | 3.00 | 1.330 ± 0.098 | 144.56 ± 1.98 | 0.920 ± 0.087 | 72.12 ± 1.33 | 14.98 ± 0.81 |
| F6 | 1:1 | 5.00 | 1.934 ± 0.145 | 26.31 ± 3.87 | 0.894 ± 0.091 | 46.54 ± 0.98 | 19.12 ± 1.44 |
| F7 | 3:1 | 1.00 | 1.16 ± 0.156 | 92.35 ± 1.19 | 2.338 ± 0.134 | 52.98 ± 0.99 | 22.67 ± 1.65 |
| F8 | 3:1 | 3.00 | 4.22 ± 0.257 | 57.05 ± 0.99 | 7.397 ± 0.219 | 38.41 ± 1.14 | 23.54 ± 1.98 |
| F9 | 3:1 | 5.00 | 6.45 ± 0.549 | 39.52 ± 1.88 | 16.321 ± 0.341 | 37.08 ± 2.13 | 25.12 ± 2.12 |

HPMC E5; Hydroxypropyl methyl cellulose E5, MDX; maltodextrin, PG; Propylene glycol TS; tensile strength, % E; percentage elongation, EM; Elastic (Young's) modulus, % D5 min; Percent drug dissolved after 5 min, MDT; In vivo mouth-dissolving time, Values are expressed as mean ± SD; # n = 3, $ n = 6.

The dependent variables (responses) including tensile strength (TS, $Y_1$), percentage elongation (% E, $Y_2$), Elastic modulus (EM, $Y_3$), in-vivo mouth dissolving time (MDT, $Y_4$), and percentage DPX dissolved after 5 minutes (% DPX, $Y_5$) were subjected to statistical analysis using Design-Expert® Software Version 11 (Stat-Ease Inc, Minneapolis, Minn., USA). ANOVA test was utilized to evaluate the impact of the variables on the studied responses at 95% level of significance. Mathematical equations corresponding to linear, two-factor interaction, and quadratic models were applied to relate the variables to the responses. The model maximizing the adjusted and predicted determination coefficients ($R^2$) was selected for each response.

The desirability function that integrates all the study responses to predict the optimum levels of the studied variables was computed to select the optimal formulation. The desired goals were maximizing the elongation percentage and percent DPX dissolved after 5 min., in addition to, minimizing in vivo mouth dissolving time, tensile strength, and elastic modulus, Table 2.

Dosage Units' Uniformity

The prepared IDBFs were split into 1×1 cm strips. Ten strips were weighed individually and the average mass of each film was recorded in milligrams. Film thickness was measured using Vernier caliper micrometer (Shanghai, China); each film's thickness was measured at six positions (two points in the center and four corners). To assess the uniformity of drug content, ten units of each of formulation were used. Each strip was dissolved in specified volume of distilled water (20 mL) and DPX content was detected spectrophotometrically at 292 nm (UV-2600 PC; Shimadzu, Kyoto, Japan). The determined drug content of the films was compared to the United States Pharmacopeial standards [30]. The acceptance value (AV) was also computed as follows:

$$AV = |M-X| + K \cdot SD$$

Where M is label claim (100%), X is the mean DPX content (%), K is the acceptability constant (2.4 for n=10), and SD is the standard deviation.

Moisture Uptake

Before conducting the study, three strips (1×3 cm) from each formulation were placed in a desiccator over $CaCl_2$ for 48 h to ensure complete dryness. The strips were then accurately weighed and directly exposed to 75% relative humidity (RH) at 25±1° C. for 7 days. The films were reweighed daily and the moisture uptake was computed as percent increase in the film's weight [31].

Mechanical Properties

The IDBFs were cut into 1×1.5 cm strips and allowed to equilibrate over $CaCl_2$ at room temperature for 7 days, then the mechanical properties were determined using Tensile Tester Machine (EZ-X, Shimadzu Co., Koyoto, Japan). Each strip was held between the two clamps of the machine and pulled at a specified rate of 5 mm/min. The force required for film breakage was recorded. Each measurement was done six times and the average determination was recorded. Tensile strength (TS) was computed by dividing the maximum load recorded at breakage by the sample cross-sectional area [32]. Percent elongation at breakage (% E) and elastic (Young's) modulus (EM) were calculated as follows:

$$\% E = \left[\frac{L - L_0}{L_0}\right] \times 100$$

$$EM = F \Big/ A\left[\frac{L_0}{L - L_0}\right]$$

Where $L_0$ and L are the length of the sample at the beginning of the experiment and its length at maximum elongation (mm), respectively. F is the maximum load at breakage (N), and A is the cross-sectional area of the film ($mm^2$) [33,34].

In-Vitro Dissolution

In vitro dissolution was performed for the prepared IDBFs using USP II dissolution test apparatus (DT 720 Series, Erweka GmbH, Germany) at 37±0.5° C. and a rotation speed of 50 rpm. A strip measuring 1×3 cm 30 mg DPX) was placed in 900 mL phosphate buffer (pH 6.8). Specified aliquots were withdrawn at preset time intervals for a period of 45 min and replaced with equal volume of fresh buffer. The samples were filtered through Millipore filter (0.45 μm) and % DPX dissolved was quantified spectrophotometrically (UV-2600 PC; Shimadzu, Kyoto, Japan) at 292 nm. Each experiment is done in triplicate.

In-Vivo Mouth-Dissolving Time (MDT) and Taste Assessment

The palatability and the time needed for the films to dissolve completely in the buccal cavity were evaluated in six healthy human volunteers. Each volunteer was administered three individual strips at a 0.5 h time intervals. The study was performed according to the ethical principles in the Declaration of Helsinki and followed the ICH GCP guidelines (Directive 75/318/EEC-1996). Every subject signed a written consent prior to starting the study. A strip of 3 cm² was placed in the volunteers' oral cavity and the time required for the films to completely dissolve was recorded. Moreover, all the participating subjects were instructed to assess the films according to taste, convenience of administration, and mouth feel using a scoring system as follows: 0 (highly satisfied), 1 (satisfied), and 2 (dissatisfied). Mouth feel and sensation was evaluated based on the residues remained in the buccal cavity following administration [32].

Effect of Storage on the Optimized DPX Instantly Dissolving Buccal Film

The selected IDBF (F4) was subjected to accelerated storage conditions according to ICH guidelines. Individual strips were wrapped in aluminum foil and subjected to storage at 40° C./75% RH for 3 months. Samples were re-evaluated for appearance, DPX content, mechanical properties, in vivo mouth dissolving time and in-vitro drug dissolution after 1 and 3 months [35]. Paired student t test was utilized to test the difference between the determined parameters before and after storage at P<0.05.

Pharmacokinetic Assessment of the Optimized DPX Instantly Dissolving Buccal Film Study Design In vivo performance of the selected DPX instantly dissolving buccal film, F4, was evaluated in male Wistar rats (n=24), weighing 250 g each, compared to DPX oral market tablet Priligy® containing DPX dose of 30 mg [26]. The experiment design was approved by the Research Ethics Committee, Faculty of Pharmacy, King Abdulaziz University, KSA (Reference number PH-118-41). The committee confirms that animal use is in compliance with the Interdisciplinary Principles and Guidelines for the Use of Animals in Research, Testing, and Education issued by the New York Academy of Sciences [36]. Rats were fasted overnight (with free access to water) prior to administration of the treatment. They were divided equally between two groups (I&II). For group I, the optimized IDBF (1×3 cm²) containing 30 mg DPX were split into two halves (1×1.5 cm²) then the two parts were applied to the two sides of the buccal cavity. Before application, the rats were subjected to short-term anesthesia (3 min) with ether to ensure that the films were maintained in the mouth cavity without passing to the gastrointestinal tract. For group II, the oral market tablets were orally administered to the rats via gastric tubing. Blood specimens were withdrawn via the tail vein in heparinized glass tubes at 0, 0.25, 0.5, 1, 2, 3, 4, 6, 8, 12, and 24 h after administration of either of the two treatments. Blood samples were centrifuged at 3000 rpm for 10 min, and the separated plasma was stored at −80° C. until analysis.

DPX Assay in Plasma

Modified method of Kim et al. [37] was adopted for the quantification of DPX concentration in rat plasma using liquid chromatography-tandem mass spectrometry with diode array detector (LC-MS/MS-DAD) analysis. An Agilent 6320 liquid chromatography-ion trap mass spectrometer (LC-IT-MS) was used for the detection of DPX. The MS system was connected to an HPLC system (Agilent 1200, Agilent Technologies, CA, USA) equipped with an autosampler and a quaternary pump. Separation was conducted on Agilent Eclipse XDB-C18 column (150 mm×4.6 mm, 5μ). The elution was performed using isocratic mobile phase comprising acetonitrile/0.1% formic acid mixture (80:20, v/v) at a flow rate of 0.5 mL·min$^{-1}$. Single positive molar ion mode was applied for detection of DPX (0-4.5 min, m/z 306.2) and the internal standard; valsartan (4.5-10 min, m/z 436.3). A calibration curve was constructed in the range of 1-1000 ng mL$^{-1}$.

Specified volumes of each of the withdrawn plasma samples was transferred to a screw-capped test tube and, mixed with a specified volume of acetonitrile and internal standard solution. The mixture was vortexed for 1 min, and then centrifuged at 5300 rpm for 7 min. An aliquot of the clear supernatant was transferred to a total recovery autosampler vial, and a specified volume was injected for LC-MS/MS-DAD analysis. Concentrations of DPX in the samples were computed based on the developed calibration curve.

Pharmacokinetic and Statistical Analysis

Non compartmental analysis was applied using PK-SOLVER. Maximum plasma concentrations ($C_{max}$, ng·mL$^{-1}$) and their corresponding time ($T_{max}$, h) were obtained from the individual plasma concentration versus time plots. The zero pharmacokinetic moment (AUC, ng·h·mL$^{-1}$) was computed as the area under the plasma concentration versus time plot. Both $C_{max}$ and AUC were expressed as mean±standard deviation, while $T_{max}$ was presented as median.

Statistical analysis was performed using Prism® (version 8.2.1, GraphPad Software Inc., La Jolla, Calif., USA) at 95% level of significance. Two-way ANOVA followed by Sidak's multiple comparisons test was applied to statistically analyze the determined plasma concentrations. The determined $C_{max}$ and AUC were statistically analyzed using unpaired t test with Welch's correction, while $T_{max}$ was analyzed using the nonparametric Mann-Whitney U test (Wilcoxon rank sum test).

Results and Discussion

Screening of Organic Acids and Cyclodextrins

DPX is characterized by pH dependent solubility that decreases as pH increases. It is reported that DPX has very low solubility in phosphate buffer pH 6.8 (0.26 μg·mL$^{-1}$), and consequently poor and slow dissolution at salivary pH [26]. Thus, physical mixtures with different organic acids and cyclodextrins were investigated for DPX dissolution enhancement in phosphate buffer pH 6.8, FIG. 1. It was evident that in absence of excipients, the drug showed very slow dissolution with percent dissolved of 2.13±0.09 and 2.89±0.06% after 2 and 15 minutes, respectively.

Figure 1:
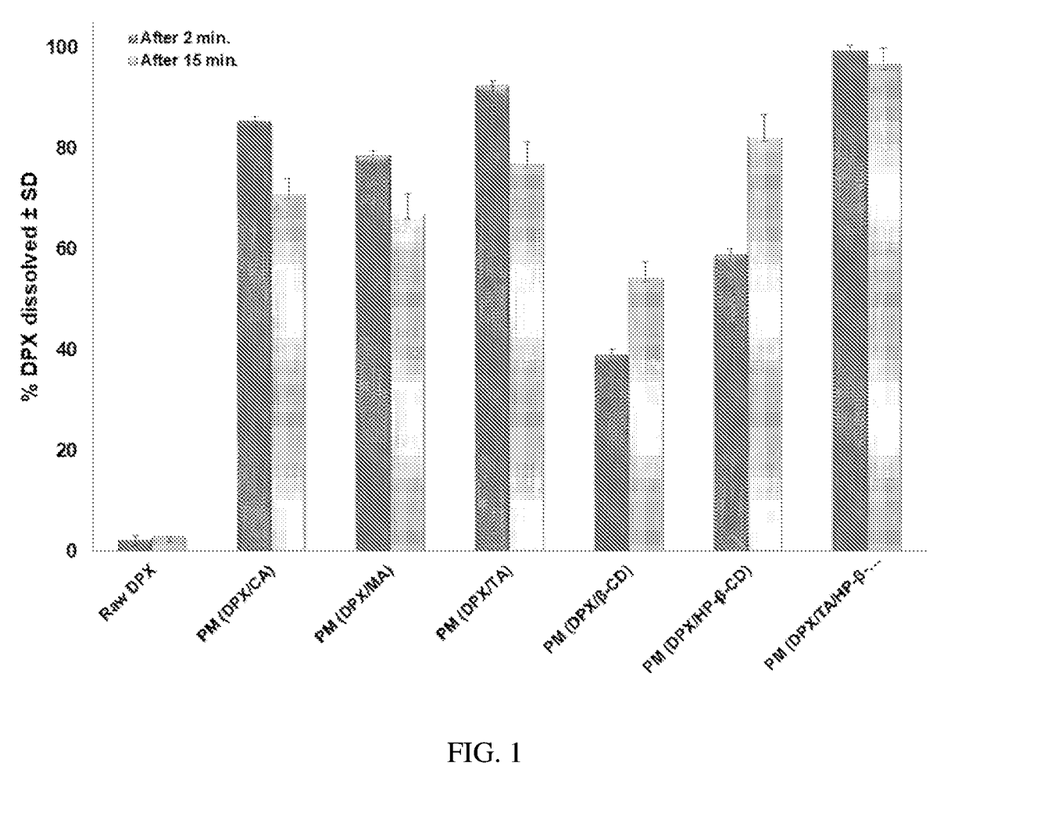
FIG. 1. Percent DPX dissolved from physical mixtures with organic acids and native cyclodextrins in comparison to raw DPX powder in phosphate buffer pH 6.8 at 37±0.5° C. (Results are presented as mean±SD, n=3).

Enhanced dissolution was observed for all the physical mixtures compared to pure drug. Regarding organic acids, the enhancement could be explained on the basis of lowering the microenvironmental pH around DPX particles. The order of enhancing drug release was as follows: TA>CA>MA. This could be interpreted on the basis of $pK_a$ values and the acidity of the used pH modifiers. The pH modifiers with lower $pk_a$ values have higher acidity, and consequently, they could have stronger modulation effect on the pH of the microenvironment around drug particles [10]. The observed order of dissolution enhancement agrees with the reported $pK_a$ values of the used pH modifiers, where TA has the lowest $pK_a$ values (2.98, 4.34), followed by CA (3.12, 4.76, 6.39) then malic acid (3.4, 5.13) [9,16].

On the other hand, the enhancement in case of cyclodextrins could be credited to their surfactant-like characteristics that lowers the interfacial tension between DPX particles and the dissolution medium, thus promoting the wetting and dissolution of the poorly soluble drug [38,39]. Moreover, the CDs rapid dissolution might result in local solubilizing action in the hydrodynamic layer surrounding drug particles in the early stages of the dissolution via the formation of drug-CD in situ inclusion complex [39]. It was observed that HP-β-CD had a greater impact on DPX dissolution compared to β-CD owing to its higher aqueous solubility and better wetting promoting effect.

It is worthy to note that although dissolution enhancement was more pronounced in case of organic acids compared to cyclodextrins after 2 min, an observed reduction in the percent dissolved was observed after 15 min. This could be attributed to the gradual rise in the pH of the drug particles microenvironment by the dilution effect of the buffered dissolution medium with consequent possible precipitation of DPX [26,40]. Thus, in an attempt to benefit from both mechanisms of dissolution, physical mixture of the drug with both TA and HP-β-CD was prepared showing significant enhancement and maintenance of drug dissolution.

Design and Preparation of DPX Instantly Dissolving Buccal Films (IDBFs)

The selection of the polymer(s) to be used in the films' development and their amounts are crucial as they represent the main component in the formulation. Polymers are responsible for imparting adequate mechanical properties to the films, and they affect the film dissolution and/or disintegration within the buccal cavity, and consequently the liberation of the drug. MDXs are mixtures of poly- and oligo-saccharides produced by starch hydrolysis that vary in their dextrose equivalent value. In this study, MDX with relatively high DE value (16.5-19.5) was selected to yield films with high solubility and low viscosity [31]. In addition, HPMC E5 is previously reported as a film forming agent for fast dissolving films [35]. Accordingly, a mixture of HPMC E5 and MDX was chosen for film development aiming at combining the advantages of the film forming ability of HPMC and the enhanced dissolution property of MDX. The mixtures were investigated in the ratios 1:3, 1:1, and 3:1.

Choosing the adequate plasticizer that is capable of imparting elasticity and good mechanical characteristics to buccal films is a crucial step in their development. The satisfactory performance of plasticizers containing hydroxyl groups with cellulose based polymers and their compatibility with MDX are previously reported [41], thus in this study, both glycerol and PG were investigated as plasticizers at a concentration range of 0 to 15%. The films prepared with propylene glycol showed appreciable flexibility at concentrations up to 5% compared to glycerin that resulted in stickier films. Concentrations of PG higher than 5% led to the formation of sticky films. The stickiness observed at higher concentrations could be credited to the oozing of excess plasticizer towards upper and lower surfaces of the film [2]; in addition, the hygroscopic nature of the plasticizer could also contribute to the observed stickiness. According to these results, PG was studied as a plasticizer in a concentration range of 1-5%. In addition, the range for the ratio of HPMC E5 (film former) to MDX (film modifier) was selected to be 1:3 to 3:1, w/w based on the physical characteristics of the preliminary films.

Based on the screening study, TA and HP-β-CD were selected to be incorporated in the prepared formulations as a pH modifier and hydrophilic solubilizer, respectively. The selected dissolution enhancing agents were incorporated at a 1:1:1 weight ratio (drug:TA:HP-β-CD) in all the prepared films.

Uniformity of Dosage Units

Mean weight and thickness of the films ranged from 65.43±4.33 to 82.63±7.13 mg and 0.24±0.02 to 0.42±0.05 mm, respectively, Table 4. The observed variability in the individual strips could be owing to the difference in ratios of HPMC E5 and MDX in the prepared films.

TABLE 4

Characterization and equilibrium moisture uptake of dapoxetine hydrochloride instantly dissolving buccal films prepared according $3^2$ full factorial design.

| Run | Weight$^\&$ (mg) | Thickness$^\$$ (mm) | Drug content (%)$^\&$ | Moisture uptake* (%)$^\#$ |
|---|---|---|---|---|
| F1 | 76.81 ± 6.11 | 0.24 ± 0.02 | 96.21 ± 1.58 | 8.68 ± 0.56 |
| F2 | 78.12 ± 5.45 | 0.29 ± 0.04 | 98.33 ± 4.12 | 12.46 ± 0.98 |
| F3 | 65.15 ± 4.33 | 0.26 ± 0.04 | 106.27 ± 2.74 | 14.90 ± 1.21 |
| F4 | 68.34 ± 6.21 | 0.30 ± 0.11 | 104.73 ± 2.91 | 8.82 ± 0.87 |
| F5 | 82.43 ± 7.13 | 0.35 ± 0.07 | 97.12 ± 1.79 | 10.17 ± 0.91 |
| F6 | 75.32 ± 6.98 | 0.32 ± 0.06 | 102.34 ± 1.52 | 11.68 ± 1.34 |
| F7 | 68.12 ± 5.87 | 0.42 ± 0.05 | 94.56 ± 3.81 | 9.61 ± 1.12 |
| F8 | 65.43 ± 5.13 | 0.39 ± 0.04 | 101.41 ± 3.14 | 12.91 ± 0.94 |
| F9 | 66.98 ± 6.09 | 0.38 ± 0.02 | 96.47 ± 1.47 | 13.67 ± 1.29 |

Values are expressed as mean ± SD; $^\$$n = 6, $^\&$n = 10.
*Equilibrium moisture uptake (after 3 days).

Regarding the content uniformity, all the prepared films complied with the compendial standards, i.e. within 90% to 110% with a relative standard deviation of ≤6% [30]. Mean DPX percent computed from six films of each formulation was in the range of 94.56±3.81 to 106.79±2.74. The relatively low standard deviations highlights the precision and the reproducibility of the casting method. In addition, the computed acceptance values were less than the Japanese Pharmacopeial (JP) accepted value of 15% [30].

Moisture Uptake

Adequate moisture percentage is required to protect the films against drying and brittleness on storage by the virtue of the plasticizing action of water. Moisture uptake studies revealed that all DPX films exhibited maximum moisture sorption after 3 days, after which no change or slight decrease in moisture uptake was recorded. The maximum moisture uptake ranged from 8.68±0.56 to 14.90±1.21%, Table 4. The moisture sorption could be credited to the presence of HPMC E5 and MDX with high DE value, where both polymers are reported to possess hygroscopic character. An overall pattern of increasing moisture sorption with increasing PG concentrations was also observed. This effect could be due to the increase in the polymers chains mobility by the virtue of insertion of the plasticizer between these chains, and consequently increasing their exposure to moisture absorption [31,32].

Statistical Analysis of the Factorial Design

Pointing out the formulation factors that might influence the drug delivery system characteristics is necessary. Factorial design has an advantage in this issue as they are able to analyze the impact of various factors synchronously. In this study, the factors and their corresponding levels were selected according to the preliminary trials as previously stated. For each response, the predicted $R^2$ of the selected model reasonably agreed with the corresponding adjusted $R^2$ (Table 5). In all responses, adequate precision with value greater than 4 confirmed that the selected model is appropriate for exploring the design space [42].

Effect of Variables on Mechanical Properties

Adequate mechanical properties are essential for the successful development of the films and their ease of handling by the patients [43]. In this study, tensile strength (TS, $Y_1$), percent elongation at break (% E, $Y_2$) and elastic modulus (EM, $Y_3$) were evaluated as indices for film' brittleness, elasticity (ductility), and stiffness, respectively [44]. The results are compiled in Table 3.

Figure 2:
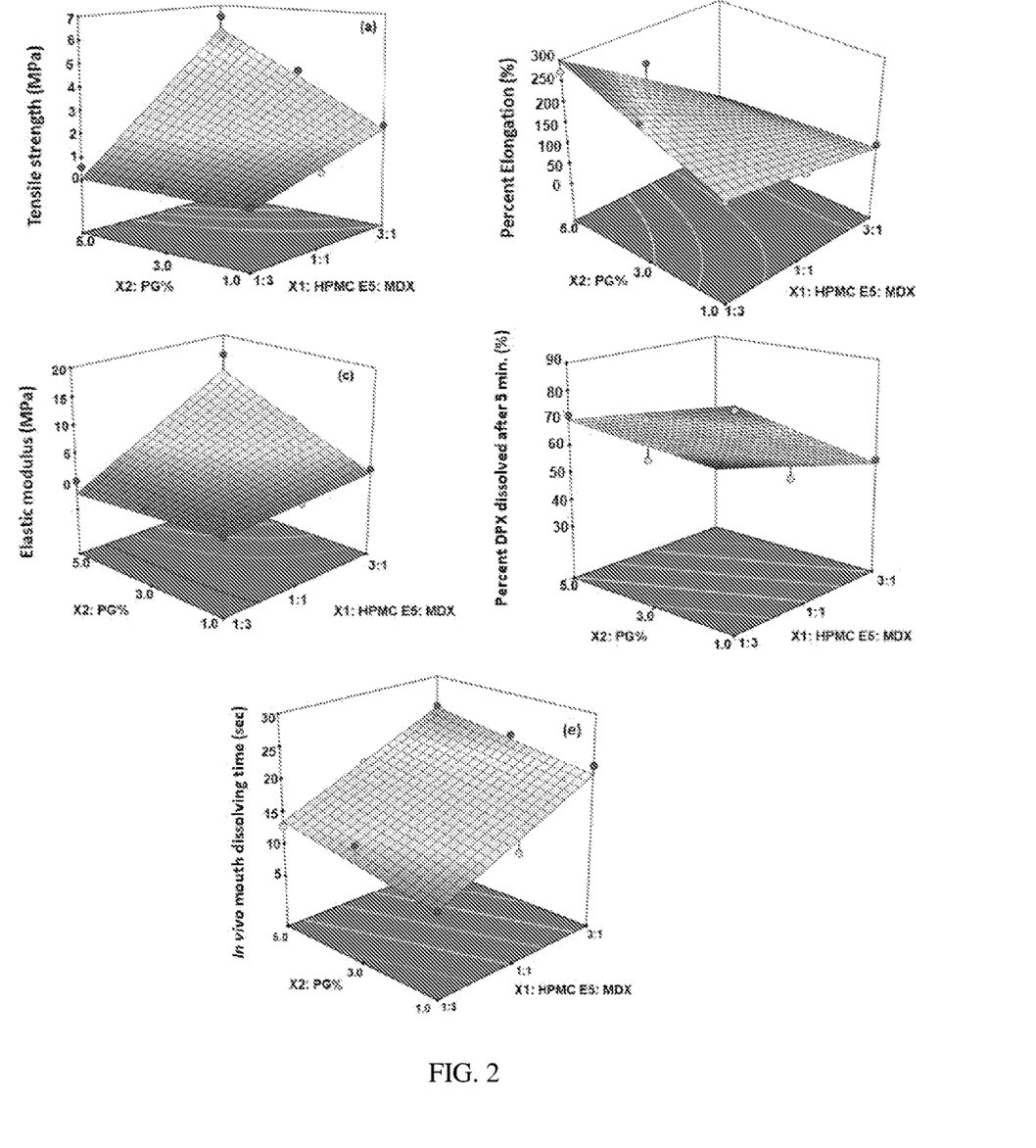
FIG. 2. Response 3D surface plot for the effect of HPMC E5:MDX ratio ($X_1$) and PG % ($X_2$) on the (a) tensile strength ($Y_1$), (b) percentage elongation ($Y_2$) at break, (c) elastic modulus ($Y_3$), percent DPX dissolved after 5 minutes ($Y_4$), and in vivo mouth dissolving time of DPX instantly-dissolving buccal films.

The response 3D-surface plots showing the influence of HPMC E5:MDX ratio ($X_1$) and PG % ($X_2$) on the films' mechanical properties are shown in FIG. 2 (a-c). The sequential model relating each of the three responses to the explored variables was suggested to be 2-factor interaction (2FI) indicating the significance of the main effects and the interactions between variables, Table 5. F-values of 21.99, 29.86, and 7.25 for $Y_1$, $Y_2$, and $Y_3$, respectively confirms the significance of the model. The equations representing the selected sequential model for each response in terms of coded factors were computed as follows:

$$Y_1 = 2.01 + 1.94X_1 + 0.9605X_2 + 0.985X_1X_2$$

$$Y_2 = 125.598 - 11.074 + 59.189X_2 - 22.343X_1X_2$$

$$Y_3 = 3.23 + 4.25X_1 + 2.37X_2 + 3.48X_1X_2$$

ANOVA revealed that the HPMC E5:MDX ratio has significant effect on all the studied mechanical properties (P=0.0010, 0.0005, and 0.0170 for TS, % E, and EM, respectively), while PG % exhibits a significant effect on both TS and % E (P=0.0196 and 0.0295, respectively). In addition, the interaction between both factors was statistically significant on the three responses (P=0.0365, 0.0127, and 0.0456 for TS, % E, and EM, respectively).

percentage DPX dissolved after 5 min ($D_{5\ min}$, $Y_4$). The suggested sequential model was the linear model indicating the significance of the main effects only. The mathematical equation that relates percent DPX dissolved after 5 min to the studied factors in terms of coded factors was computed as follows:

$$Y_4 = 60.65 - 17.25 - 8.30X_2$$

ANOVA revealed that both HPMC E5:MDX and PG % had significant impact of on DPX dissolution from the films (P=0.0004 and 0.0133, respectively). The effect of polymers ratio on drug dissolution was more pronounced than that of plasticizer concentration as evident by the lower P-value and the higher coefficient of $X_1$ compared to $X_2$. FIG. 2d shows that $D_{5\ min}$ significantly decreases with increasing both HPMC E5:MDX ratio and PG %. The effect of polymers ratio could be explained on the basis of varying concentrations of both HPMC E5 and MDX simultaneously. At higher HPMC levels, viscous gel layer formation surrounding drug particles due to the closer contact of the polymer chains could result in reduced mobility of the drug within the

TABLE 5

Output data of the analysis of $3^2$ factorial design used for the formulation of DPX instantly dissolving buccal films.

| Response | Model | P-value | $R^2$ | Adjusted $R^2$ | Predicted $R^2$ | Adequate precision | Significant factors and interactions |
|---|---|---|---|---|---|---|---|
| $Y_1$: TS (MPa) | 2FI | 0.0026 | 0.9295 | 0.8873 | 0.7176 | 12.5912 | $X_1, X_2, X_1X_2$ |
| $Y_2$: % E (%) | 2FI | 0.0013 | 0.9471 | 0.9154 | 0.7514 | 15.6532 | $X_1, X_2, X_1X_2$ |
| $Y_3$: EM (MPa) | 2F1 | 0.0287 | 0.813 | 0.7008 | 0.5006 | 7.8320 | $X_1, X_1X_2$ |
| $Y_4$: % $D_{5min}$ (%) | Linear | 0.0006 | 0.9144 | 0.8859 | 0.8652 | 15.1142 | $X_1, X_2$, |
| $Y_5$: In vivo MDT (sec) | Linear | 0.0006 | 0.9173 | 0.8897 | 0.8424 | 14.7436 | $X_1, X_2$, |

TS; Tensile strength, % E; Percent elongation at break, EM; Elastic (Young's modulus), % $D_{5min}$; Percent drug dissolved after 5 mM, MDT; In vivo mouth dissolving time FIG. 2 illustrates that increasing HPMC:MDX ratio led to significant increase in TS and EM accompanied by marked decrease in % E and vice-versa. This result agrees with previous work that reported hard and brittle nature for films made with HPMC alone. On the other hand, the simultaneous increase in MDX (with high DE value) concentration with decreasing HPMC concentration could result in higher flexibility and ductility to the films [31,45].

In contrast, increasing PG % was accompanied by significant reduction in the TS and increase in the % E of the prepared films. This could be explained on the basis of the plasticizing action of PG. Plasticizers are reported to embed themselves among the polymer chains, and thus, cause the disruption of polymer chains interaction leading to increase in their mobility [31]. This action is expected to impart increased ductility and decreased stiffness for the films with increasing plasticizer concentration [32,43].

Effect of Variables on In Vitro Dissolution

Figure 3:
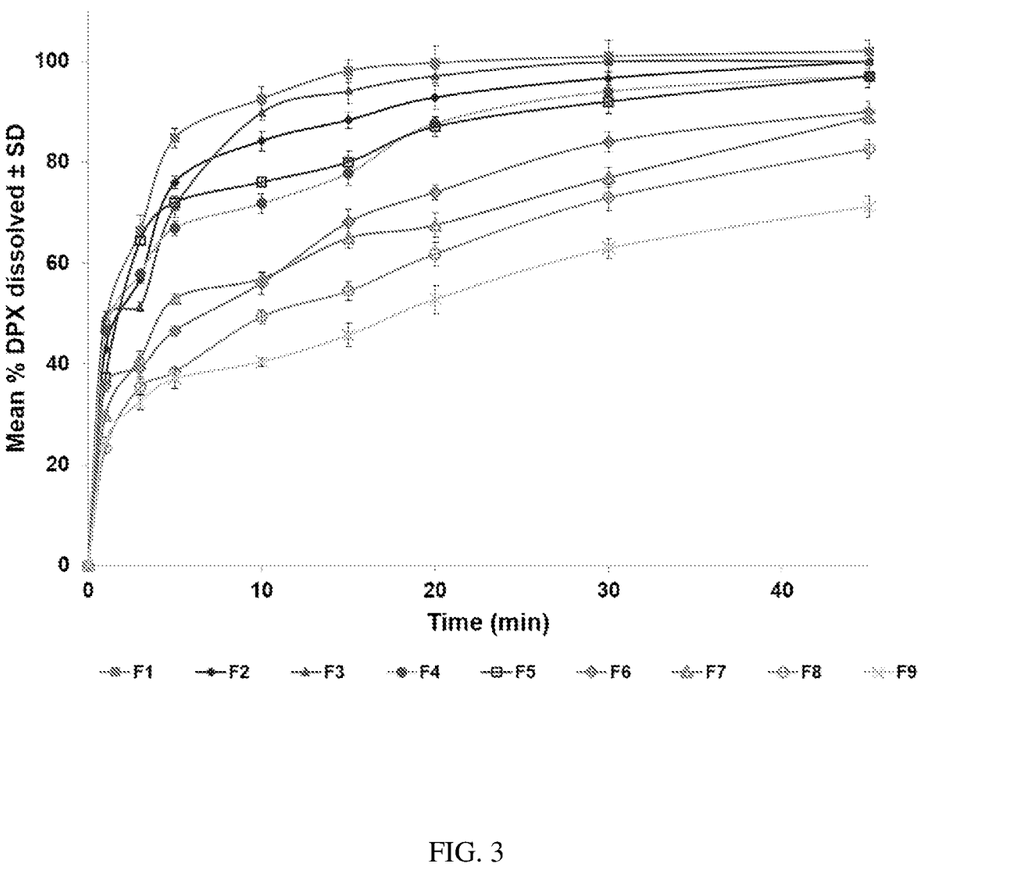
FIG. 3. In vitro dissolution profiles of DPX instantly-dissolving buccal films in phosphate buffer pH 6.8 at 37±0.5° C. (Results are presented as mean±SD, n=3).

In-vitro dissolution profiles of DPX instantly dissolving buccal films in phosphate buffer pH 6.8 exhibited remarkable differences among formulations as depicted in FIG. 3. Percent drug dissolved after 5 minutes ranged from 37.08±2.13 to 84.76±3.98%. For further evaluation for the source of this variation, statistical analysis for percent DPX dissolved after 5 min was performed using ANOVA. F-value of 32.06 affirms the significance of the model, where there is only a 0.06% chance that this value could be large due to noise. FIG. 2d illustrates the response 3D-surface plot of the effect of HPMC E5:MDX ($X_1$) and PG % ($X_2$) on the formed gel layer, and consequently reduced dissolution rate [46]. Similar effect for increasing HPMC concentration was previously reported by Abdelbary et al. [35]. On the other hand, increasing MDX resulted in increased drug dissolution owing to its high aqueous solubility that contributes to enhancing DPX dissolution from the prepared films [31].

Effect of Variables on In-Vivo Mouth-Dissolving Time (MDT) and Palatability Studies All the prepared formulations showed short dissolving time in the saliva of less than 30 s, however, marked variations of MDT were observed among formulations ranging from 9.67±0.56 to 25.12±2.12 s, Table 3. The effects of HPMC E5:MDX ($X_1$) and PG % ($X_2$) on the in-vivo MDT ($Y_5$) is displayed in the response 3D-surface plot, FIG. 2e. The suggested sequential model was linear rather than 2FI indicating the insignificance of the interaction between polymers ratio and PG % on MDT. F-value of 33.26 affirms the significance of the model indicating there is only a 0.06% chance that this value could be large owing to noise. The linear equation depicting the relation between in-vivo MDT ($Y_5$) and the investigated variables was computed as:

$$Y_5 = 17.22 + 5.66X_1 + 2.02X_2$$

Statistical treatment of the data using ANOVA showed a significant influence for both polymers ratio and PG % on in vivo MDT (P=0.0003 and 0.0335, respectively). The impact of polymers ratio was more obvious than that of plasticizer concentration as evident by the lower P-value and the higher coefficient of $X_1$ compared to $X_2$. It was evident that MDT increases with increasing HPMC E5:MDX. This could be ascribed to viscous gel layer formation upon contacting saliva at higher HPMC concentration with consequent hindrance of further fluids penetration and retardation of the films' dissolution in the oral cavity. Similar effect for increasing HPMC concentration on the films' disintegration time was reported in previous studies [35,47]. In addition, the increase in MDX concentration at lower HPMC E5:MDX ratios could contribute to decreasing the MDT by the virtue of the high aqueous solubility of MDX that could facilitate the fluid penetration into the films [31,32]. Furthermore, the observed significant decreased MDT with increasing plasticizer concentration has been previously reported and was related to the reduced tensile strength of the films [45,48].

Regarding the in-vivo palatability study, all the formulations showed satisfactory results for with a score ranging from 0 (highly satisfied) to 1 (satisfied) for the taste and a score of 0 (highly satisfied) for the convenience of administration and mouth feel. Although PG is reported to have a bitter taste, all the films were satisfactory with respect to taste owing to the added sweetener, saccharin, and the flavoring agent, orange oil. In addition, the presence of MDX might contribute to improving the films' palatability due to its sweetening action [2,32]. The satisfactory results with respect to mouth feel of all films assures complete and rapid dissolution in the mouth.

Selection of the Optimized DPX Instantly Dissolving Buccal Film

Desirability function was applied for selection of the optimized DPX instantly dissolving buccal film from the prepared films according to the $3^2$ factorial design. The criteria set for selection were attaining maximum flexibility and in vitro dissolution, in addition to minimum in vivo mouth dissolving duration as presented in Table 2. It was found that DPX film F4 prepared at a ratio of 1:1, w/w HPMC E5:MDX and 1% PG fulfilled the required criteria with a desirability value of 0.802. Thus this formulation was selected for further stability studies and in vivo assessment. It is worthy to note that although the formulation F1-F3 prepared at a ratio of 1:3, w/w HPMC E5:MDX exhibited better desirability values, yet, they were excluded from further investigations due to their high stickiness that could result from the relatively low concentration of the film former HPMC E5.

Effect of Storage on the Optimized DPX IDBF

Upon storage of the selected DPX film, F4, at the specified conditions, the stored films showed no appreciable changes in the physical appearance or characteristics. The results are compiled in Table 6. Paired student t test revealed no significant difference between the parameters of the fresh films and the stored ones at P<0.05.

TABLE 6

Effect of storage on the characteristics of the selected optimized DPX instantly dissolving buccal film (F4) at 40° C./75% RH for 3 months.

|  | Fresh Films | After 1 month | After 3 months |
| --- | --- | --- | --- |
| Weights[&] (mg) | 68.34 ± 6.21 | 69.11 ± 4.65 | 70.14 ± 5.87 |
| Thickness[$] (mm) | 0.30 ± 0.11 | 0.31 ± 0.14 | 0.31 ± 0.37 |
| Drug content (%)[&] | 104.73 ± 2.91 | 99.43 ± 4.11 | 98.32 ± 2.89 |
| TS[$] (MPa) | 0.811 ± 0.077 | 0.823 ± 0.091 | 0.834 ± 0.106 |
| % E[$] (%) | 115.34 ± 1.56 | 113.45 ± 1.59 | 112.67 ± 2.21 |
| EM[$] (MPa) | 0.703 ± 0.065 | 0.725 ± 0.073 | 0.740 ± 0.098 |
| $D_{5min}$[#] (%) | 66.91 ± 2.45 | 65.14 ± 3.27 | 64.99 ± 3.19 |
| MDT[$] (sec) | 13.15 ± 1.77 | 13.99 ± 2.11 | 14.65 ± 1.98 |

TS; Tensile strength, % E; Percent elongation at break, EM; Elastic (Young's) modulus, % $D_{5min}$; Percent drug dissolved after 5 min, In vivo MDT; In vivo mouth dissolving time
*Values are expressed as mean ± SD; [#]n = 3, [$]n = 6, [&]n = 1

In addition, there was also no significant change in the dissolution profile in phosphate buffer pH 6.8 (data not shown) as evidenced by the computed similarity factor $f_2$ between the fresh and the stored films' dissolution profiles [49]. The computed $f_2$ values of 69.04 and 62.52 after 1 and 3 months, respectively, could indicate adequate relative stability of the formulations.

Pharmacokinetic Assessment of the Optimized DPX Instantly Dissolving Buccal Film The relationship between DPX concentrations spiked in plasma and peak area ratios (DPX/IS) showed good linearity with determination coefficient ($R^2$) of 0.9984. The assay showed acceptable intra- and inter-day precision with CV % of <9% and <13%, respectively. The assay accuracy was also acceptable with % relative error ranging from 3.38-12.89%. Mean DPX concentrations in rats' plasma versus time following buccal administration of the optimized DPX IDBF (F4) compared to oral reference product are graphically plotted in FIG. 4.

Figure 4:
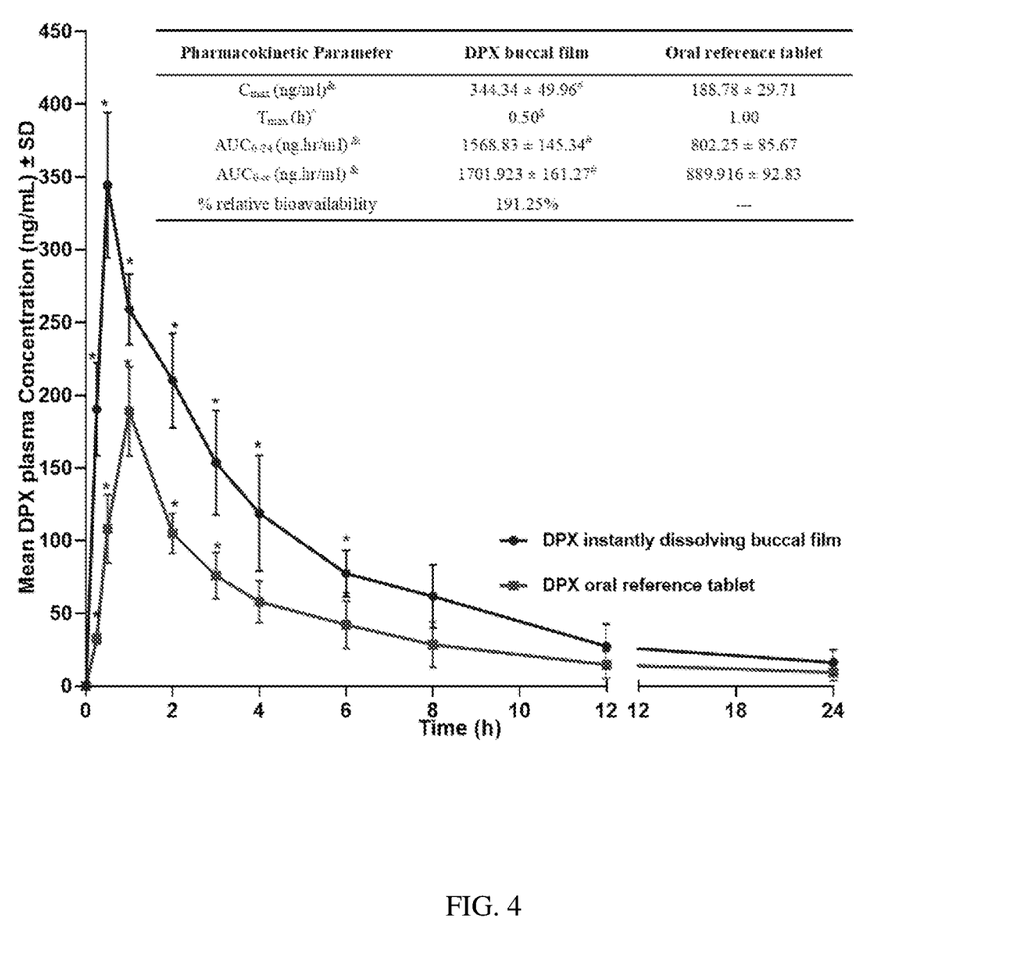
FIG. 4. Mean DPX plasma concentration versus time following buccal administration of optimized instantly dissolving film compared to oral reference tablet in rats and computed in vivo pharmacokinetic parameters (Inset table). &Data represent the mean value±standard deviation (SD), n=12, Δ Data represent the median, n=12, *Significant at $P<0.05$, test of significance using Two-way ANOVA, Sidak's multiple comparisons test, Significant at $p<0.05$, test of significance using unpaired t test (two-tailed) with Welch's correction, $Significant at $p<0.05$, test of significance using Mann-Whitney test.

Compared to the oral reference tablet, the optimized DPX film demonstrated a significantly higher $C_{max}$ and AUC (P=0.0125 and 0.0231, respectively) and a relative bioavailability of 191.25%, FIG. 4 (Inset table). The significant enhanced absorption of DPX following buccal administration of the optimized IDBF could be credited to the dual solubilizing action of both the pH modifier (TA) and the hydrophilic solubilizer (HP-β-CD) that was previously discussed under section 3.1. In addition, avoiding the hepatic first pass effect of the drug via the buccal route could significantly contribute to increasing the drug's absorption. In addition, the film demonstrated a significantly shorter T. (P=0.0317) than the oral market tablets that could be explained on the basis of rapid dissolution of the film in the oral cavity with consequent rapid absorption via the highly vascular oral mucosa.

The buccal formulation developed in this Example resulted in enhanced bioavailability of dapoxetine with relative bioavailability of 191.25%. This dramatic enhancement could lead to reduction of dose and any possible undesired side effects.

Conclusion

The objective of this work was to improve the bioavailability of DPX via the formulation of an instantly dissolving buccal film with a dual mechanism for enhancement of drug dissolution (the use of both acidic pH modifier and hydrophilic cyclodextrin). TA and HP-β-CD were selected for the drug solubilization based on the screening study. $3^2$ full factorial design was successfully applied for the development and optimization of the films. The film prepared utilizing HPMC E5:MDX (1:1, w/w) and 1% PG was selected as the optimum film based on the desirability function. The selected film showed satisfactory physical and mechanical properties, high in-vivo dissolution, and rapid in vivo mouth dissolution. In addition, it exhibits significantly higher and more rapid drug absorption compared to the oral reference product in rats. Therefore, the developed formulation is a new delivery system for the drug with expected enhanced patient compliance and improved bioavailability owing to drug dissolution enhancement and avoidance of first pass effect.

Example 2

We have further tested formulations lacking the tartaric acid and hydroxypropyl beta cyclodextrin combination which shows that this combination leads to a synergistic effect (see Table 7).

TABLE 7

Composition and in vivo evaluation of claimed DPX buccal films versus buccal formulations with individual components

|  | Claimed DPX films | F001 | F002 | F003 | Market Oral Tablet |
|---|---|---|---|---|---|
| Composition | DPX 30 mg HPMC: Maltodextrin (1:1, total conc. 16%) PG 1% HP-beta-CD Tartaric acid *(DPX: CD: TA, 1:1:1) | DPX 30 mg HPMC: Maltodextrin (1:1, total conc. 16%) PG 1% Tartaric acid *(DPX: TA, 1:1:1) | DPX 30 mg HPMC: Maltodextrin (1:1, total conc. 16%) HP-beta-CD *(DPX: CD, 1:1) | DPX 30 mg HPMC: Maltodextrin (1:1, total conc. 16%) |  |
| $C_{max}$ (ng/ml)[&] | 344.34 ± 49.96 | 195.19 ± 17.34 | 201.87 ± 21.34 | 191.81 ± 16.26 | 188.78 ± 29.71 |
| $T_{max}$ (h)[^] | 0.50 | 0.50 | 0.50 | 1.0 | 1.00 |
| $AUC_{0-24}$ (ng · hr/ml)[&] | 1568.83 ± 145.34 | 840.13 ± 76.91 | 851.45 ± 79.79 | 824.56 ± 81.51 | 802.25 ± 85.67 |
| $AUC_{0-\infty}$ (ng · hr/ml)[&] | 1701.923 ± 161.27 | 953.56 ± 98.71 | 972.58 ± 99.39 | 932.83 ± 87.41 | 889.91 ± 92.83 |
| % relative bioavailability | 191.25% | 107.15% | 109.28% | 104.82% |  |

[&]Data represent the mean value ± standard deviation (SD), n = 12
[^]Data represent the median In view of this data, it is evident that the combined use of tartaric acid and HP beta cyclodextrin in the films produced surprisingly marked enhancement in the bioavailability compared to the use of individual components. The film without either component had a relative bioavailability of ~104% while the addition of either component individually only provided a modest increase (~107% with tartaric acid and ~109% with HP beta cyclodextrin). However, the combination provided unexpectedly superior bioavailability at 191.25%.

Acknowledgement

This project was funded by the Deanship of Scientific Research (DSR) at King Abdulaziz University, Jeddah, under grant no. RG-3-166-38. The inventors, therefore, acknowledge with thanks DSR for technical and financial support.

REFERENCES

[1] Kathpalia H, Gupte A. An introduction to fast dissolving oral thin film drug delivery systems: a review. Curr Drug Deliv 2013; 10:667-84.
[2] Fahmy R H, Badr-Eldin S M. Novel delivery approach for ketotifen fumarate: Dissofilms formulation using 32 experimental design: In vitro/in vivo evaluation. Pharm Dev Technol 2014; 19. doi:10.3109/10837450.2013.800108.
[3] Hosny K M, El-Say K M, Ahmed O A. Optimized sildenafil citrate fast orodissolvable film: A promising formula for overcoming the barriers hindering erectile dysfunction treatment. Drug Deliv 2016; 23:355-61. doi: 10.3109/10717544.2014.916763.
[4] Shimoda H, Taniguchi K, Nishimura M, Matsuura K, Tsukioka T, Yamashita H, et al. Preparation of a fast dissolving oral thin film containing dexamethasone: a possible application to antiemesis during cancer chemotherapy. Eur J Pharm Biopharm 2009; 73:361-5. doi: 10.1016/j.ejpb.2009.08.010.
[5] Senta-Loys Z, Bourgeois S, Valour J P, Briancon S, Fessi H. Orodispersible films based on amorphous solid dispersions of tetrabenazine. Int J Pharm 2017; 518:242-52. doi:10.1016/j.ijpharm.2016.12.036.
[6] Dixit R P, Nagarsenker M S. Self-nanoemulsifying granules of ezetimibe: design, optimization and evaluation. Eur J Pharm Sci 2008; 35:183-92. doi:10.1016/j.ejps.2008.06.013.
[7] Badr-Eldin S M, Ahmed T A, Ismail H R. Aripiprazole-cyclodextrin binary systems for dissolution enhancement: Effect of preparation technique, cyclodextrin type and molar ratio. Iran J Basic Med Sci 2013; 16.
[8] Kwon H, Heo E-J, Kim Y-H, Kim S, Hwang Y-H, Byun J-M, et al. Development and Evaluation of Poorly Water-Soluble Celecoxib as Solid Dispersions Containing Nonionic Surfactants Using Fluidized-Bed Granulation. Pharmaceutics 2019; 11:136. doi:10.3390/pharmaceutics11030136.
[9] Adachi M, Hinatsu Y, Kusamori K, Katsumi H, Sakane T, Nakatani M, et al. Improved dissolution and absorption of ketoconazole in the presence of organic acids as pH-modifiers. Eur J Pharm Sci 2015; 76:225-30. doi: 10.1016/j.ejps.2015.05.015.
[10] Kojo Y, Matsunaga S, Suzuki H, Taniguchi C, Kawabata Y, Wada K, et al. Improved Dissolution of Dipyridamole with the Combination of pH-Modifier and Solid Dispersion Technology. Chem Pharm Bull Pharm Bull 2017; 65:426-31. doi:10.1248/cpb.c16-00714.

[11] Onoue S, Inoue R, Taniguchi C, Kawabata Y, Yamashita K, Wada K, et al. Improved dissolution and pharmacokinetic behavior of dipyridamole formulation with microenvironmental pH-modifier under hypochlorhydria. Int J Pharm 2012; 426:61-6. doi:10.1016/j.ijpharm.2012.01.014.

[12] Bi M, Kyad A, Alvarez-Nunez F, Alvarez F. Enhancing and Sustaining AMG 009 Dissolution from a Bilayer Oral Solid Dosage Form via Microenvironmental pH Modulation and Supersaturation. AAPS PharmSciTech 2011; 12:1401-6. doi:10.1208/s12249-011-9710-2.

[13] Bassi P, Kaur G. pH modulation: a mechanism to obtain pH-independent drug release. Expert Opin Drug Deliv 2010; 7:845-57. doi:10.1517/17425247.2010.491508.

[14] Taniguchi C, Kawabata Y, Wada K, Yamada S, Onoue S. Microenvironmental pH-modification to improve dissolution behavior and oral absorption for drugs with pH-dependent solubility. Expert Opin Drug Deliv 2014; 11:505-16. doi:10.1517/17425247.2014.881798.

[15] Ploen J, Andersch J, Heschel M, Leopold C S. Citric acid as a pH-modifying additive in an extended release pellet formulation containing a weakly basic drug. Drug Dev Ind Pharm 2009; 35:1210-8. doi:10.1080/03639040902882256.

[16] Choi J S, Kwon S H, Lee S E, Jang W S, Byeon J C, Jeong H M, et al. Use of acidifier and solubilizer in tadalafil solid dispersion to enhance the in vitro dissolution and oral bioavailability in rats. Int J Pharm 2017; 526:77-87. doi:10.1016/j.ijpharm.2017.04.056.

[17] Singh S, Parikh T, Sandhu H K, Shah N H, Malick A W, Singhal D, et al. Supersolubilization and amorphization of a model basic drug, haloperidol, by interaction with weak acids. Pharm Res 2013; 30:1561-73. doi:10.1007/s11095-013-0994-7.

[18] Shah A, Serajuddin A T M. Conversion of solid dispersion prepared by acid-base interaction into free-flowing and tabletable powder by using Neusilin® US2. Int J Pharm 2015; 484:172-80. doi:10.1016/j.ijpharm.2015.02.060.

[19] Parikh T, Sandhu H K, Talele T T, Serajuddin A T M. Characterization of Solid Dispersion of Itraconazole Prepared by Solubilization in Concentrated Aqueous Solutions of Weak Organic Acids and Drying. Pharm Res 2016; 33:1456-71. doi:10.1007/s11095-016-1890-8.

[20] Loftsson T, Duchene D. Cyclodextrins and their pharmaceutical applications. Int J Pharm 2007; 329:1-11. doi:10.1016/j.ijpharm.2006.10.044.

[21] Sharma N, Baldi A. Exploring versatile applications of cyclodextrins: an overview. Drug Deliv 2014:1-19. doi:10.3109/10717544.2014.938839.

[22] Russo A, Capogrosso P, Ventimiglia E, La Croce G, Boeri L, Montorsi F, et al. Efficacy and safety of dapoxetine in treatment of premature ejaculation: An evidence-based review. Int J Clin Pract 2016; 70:723-33. doi:10.1111/ijcp.12843.

[23] Waldinger M D. Drug treatment options for premature ejaculation. Expert Opin Pharmacother 2018; 19:1077-85. doi:10.1080/14656566.2018.1494725.

[24] McMahon C G. Dapoxetine: a new option in the medical management of premature ejaculation. Ther Adv Urol 2012; 4:233-51. doi:10.1177/1756287212453866.

[25] Andersson K E, Mulhall J P, Wyllie M G. Pharmacokinetic and pharmacodynamic features of dapoxetine, a novel drug for "on-demand" treatment of premature ejaculation. BJU Int 2006; 97:311-5. doi:10.1111/j.1464-410X.2006.05911.x.

[26] Fouad S A, Shamma R N, Basalious E B, El-Nabarawi M A, Tayel S A. Novel instantly-soluble transmucosal matrix (ISTM) using dual mechanism solubilizer for sublingual and nasal delivery of dapoxetine hydrochloride: In-vitro/in-vivo evaluation. Int J Pharm 2016; 505: 212-22. doi:10.1016/j.ijpharm.2016.04.006.

[27] Fouad S A, Shamma R N, Basalious E B, El-Nabarawi M M, Tayel S A. Novel instantly-dispersible nanocarrier powder system (IDNPs) for intranasal delivery of dapoxetine hydrochloride: in-vitro optimization, ex-vivo permeation studies, and in-vivo evaluation. Drug Dev Ind Pharm 2018; 44:1443-50. doi:10.1080/03639045.2018.1459675.

[28] Liew K Bin, Peh K K. Investigation on the effect of polymer and starch on the tablet properties of lyophilized orally disintegrating tablet. Arch Pharm Res 2015. doi: 10.1007/s12272-014-0542-y.

[29] El-Refai K, Teaima M H, El-Nabarawi M A. Dual-purpose vardenafil hydrochloride/dapoxetine hydrochloride orodispersible tablets: in vitro formulation/evaluation, stability study and in vivo comparative pharmacokinetic study in healthy human subjects. Drug Dev Ind Pharm 2018; 44:988-1000. doi:10.1080/03639045.2018.1427761.

[30] USP 41-NF36. (905) Uniformity of Dosage Units. United States Pharmacop. Natl. Formul., Rockville, Md.: The united States Pharmacopeial Convention, United Book Press, Inc.; 2018, p. 6637.

[31] ElMeshad A N, El Hagrasy A S. Characterization and optimization of orodispersible mosapride film formulations. AAPS PharmSciTech 2011; 12:1384-92. doi: 10.1208/s12249-011-9713-z.

[32] Cilurzo F, Cupone I E, Minghetti P, Selmin F, Montanari L. Fast dissolving films made of maltodextrins. Eur J Pharm Biopharm 2008; 70:895-900. doi:10.1016/j.ejpb.2008.06.032.

[33] Fahmy R H, Badr-Eldin S M. Novel delivery approach for ketotifen fumarate: dissofilms formulation using $3^2$ experimental design: in vitro/in vivo evaluation. Pharm Dev Technol 2014; 19:521-30. doi:10.3109/10837450.2013.800108.

[34] Li-Li X, ALi-Li S, Qing-Ri C, Wei-Juan X, Yue C, Xiao-Yin Z, et al. Formulation and in vitro characterization of novel sildenafil citrateloaded polyvinyl alcohol-polyethylene glycol graft copolymer-based orally dissolving films. Int J Pharm 2014; 473:398-406.

[35] Abdelbary A, Bendas E R, Ramadan A A, Mostafa D A. Pharmaceutical and pharmacokinetic evaluation of a novel fast dissolving film formulation of flupentixol dihydrochloride. AAPS PharmSciTech 2014; 15:1603-10. doi: 10.1208/s12249-014-0186-8.

[36] New York Academy of Sciences. Interdisciplinary principles and guidelines for the use of animals in research, testing, and education. A report of the Ad Hoc Committee on Animal Research., New York: New York Academy of Sciences; 1988.

[37] Kim T K, Kim I S, Hong S H, Choi Y K, Kim H, Yoo H H. Determination of dapoxetine in rat plasma by ultra-performance liquid chromatography—tandem mass spectrometry. J Chromatogr B 2013; 926:42-6. doi: 10.1016/j.jchromb.2013.03.002.

[38] Moyano J R, Ginés J M, Arias M J, Rabasco A M. Study of the dissolution characteristics of oxazepam via complexation with β-cyclodextrin. Int J Pharm 1995; 114:95-102. doi:10.1016/0378-5173(94)00220-Y.

[39] Badr-Eldin S M, Elkheshen S A, Ghorab M M. Inclusion complexes of tadalafil with natural and chemically modified β-cyclodextrins. I: Preparation and in-vitro evaluation. Eur J Pharm Biopharm 2008; 70. doi:10.1016/j.ejpb.2008.06.024.

[40] Senta-Loys Z, Bourgeois S, Valour J-P, Briancon S, Fessi H. Orodispersible films based on amorphous solid dispersions of tetrabenazine. Int J Pharm 2017; 518:242-52. doi:10.1016/j.ijpharm.2016.12.036.

[41] Dixit R P, Puthli S P. Oral strip technology: Overview and future potential. J Control Release 2009; 139:94-107. doi:10.1016/j.jconrel.2009.06.014.

[42] Al-Mahallawi A M, Abdelbary A A, Aburahma M H. Investigating the potential of employing bilosomes as a novel vesicular carrier for transdermal delivery of tenoxicam. Int J Pharm 2015; 485:329-40. doi:10.1016/j.ijpharm.2015.03.033.

[43] Jantrawut P, Chaiwarit T, Jantanasakulwong K, Brachais C H, Chambin O. Effect of plasticizer type on tensile property and in vitro indomethacin release of thin films based on low-methoxyl pectin. Polymers (Basel) 2017; 9. doi:10.3390/polym9070289.

[44] Batista P, Castro P, Madureira A R, Sarmento B, Pintado M. Development and characterization of chitosan microparticles-in-films for buccal delivery of bioactive peptides. Pharmaceuticals 2019; 12:1-15. doi:10.3390/ph12010032.

[45] Liew K Bin, Tan Y T F, Peh K-K. Effect of polymer, plasticizer and filler on orally disintegrating film. Drug Dev Ind Pharm 2014; 40:110-9. doi:10.3109/03639045.2012.749889.

[46] Jadhav Y G, Galgatte U C, Chaudhari P D. Overcoming poor solubility of dimenhydrinate: Development, optimization and evaluation of fast dissolving oral film. Adv Pharm Bull 2018; 8:721-5. doi:10.15171/apb.2018.081.

[47] Dangre P V., Phad R D, Surana S J, Chalikwar S S. Quality by design (QbD) assisted fabrication of fast dissolving buccal film for clonidine hydrochloride: Exploring the quality attributes. Adv Polym Technol 2019; 2019. doi:10.1155/2019/3682402.

[48] Bala R, Sharma S. Formulation optimization and evaluation of fast dissolving film of aprepitant by using design of experiment. Bull Fac Pharmacy, Cairo Univ 2018; 56:159-68. doi:10.1016/j.bfopcu.2018.04.002.

[49] Costa P, Sousa Lobo J M. Modeling and comparison of dissolution profiles. Eur J Pharm Sci 2001; 13:123-33. doi:10.1016/50928-0987(01)00095-1.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A buccal film comprising:
25-35 mg tartaric acid,
hydroxypropyl-beta-cyclodextrin,
hydroxypropyl methylcellulose (HPMC),
maltodextrin, and
25-35 mg dapoxetine hydrochloride,
wherein a ratio of hydroxypropyl-beta-cyclodextrin to tartaric acid is 1:1.

2. The film of claim 1, further comprising 1-5% propylene glycol.

3. The film of claim 1, wherein the ratio of HPMC to maltodextrin is from 1:3 to 3:1.

4. The film of claim 1, wherein the ratio of HPMC to maltodextrin is 1:1.

5. The film of claim 1, wherein the maltodextrin has a dextrose equivalent value of 16.5-19.5.

6. The film of claim 1, wherein the film comprises 60-180 mg of HPMC and 60-180 mg of maltodextrin.

7. A method of improving bioavailability of dapoxetine hydrochloride, comprising a step of buccally administering the film of claim 1 to a subject in need thereof.

8. The method of claim 7, wherein the film further comprises 1-5% propylene glycol.

9. The method of claim 7, wherein the ratio of HPMC to maltodextrin is from 1:3 to 3:1.

10. The method of claim 7, wherein the ratio of HPMC to maltodextrin is 1:1.

11. The method of claim 7, wherein the maltodextrin has a dextrose equivalent value of 16.5-19.5.

12. The method of claim 7, wherein the film comprises 60-180 mg of HPMC and 60-180 mg of maltodextrin.

* * * * *